United States Patent [19]
Johnson

[11] Patent Number: 5,683,404
[45] Date of Patent: Nov. 4, 1997

[54] CLAMP AND METHOD FOR ITS USE

[75] Inventor: Wesley D. Johnson, Chanhassen, Minn.

[73] Assignee: Metagen, LLC, Menomonie, Wis.

[21] Appl. No.: 658,757

[22] Filed: Jun. 5, 1996

[51] Int. Cl.[6] ................................................ A61B 17/122
[52] U.S. Cl. .................................................. 606/151; 606/74
[58] Field of Search ............................ 606/74, 139, 140,
606/151, 157, 213; 24/17 A, 19, 20 R,
21, 22, 23 W, 20 CW, 20 W

[56] References Cited

U.S. PATENT DOCUMENTS

| | | |
|---|---|---|
| 3,786,806 | 1/1974 | Johnson et al. . |
| 4,037,324 | 7/1977 | Andreasen . |
| 4,119,091 | 10/1978 | Partridge ............................ 606/74 |
| 4,665,906 | 5/1987 | Jervis . |
| 5,035,712 | 7/1991 | Hoffman . |
| 5,385,583 | 1/1995 | Cotrel . |
| 5,405,347 | 4/1995 | Lee et al. . |
| 5,423,820 | 6/1995 | Miller et al. . |
| 5,466,238 | 11/1995 | Lin . |
| 5,474,553 | 12/1995 | Baumgart . |
| 5,474,557 | 12/1995 | Mai . |
| 5,476,462 | 12/1995 | Allard et al. . |
| 5,476,464 | 12/1995 | Metz-Stavenhagen et al. . |
| 5,476,465 | 12/1995 | Preissman . |
| 5,507,826 | 4/1996 | Besselink et al. . |
| 5,571,105 | 11/1996 | Gundolf ............................ 606/74 |

*Primary Examiner*—Michael Buiz
*Assistant Examiner*—Daphna Shai
*Attorney, Agent, or Firm*—Fredrikson & Byron

[57] ABSTRACT

A clamp is provided for fastening to an article that has a fastenable portion of a predetermined shape and size. The clamp body is formed at least in part of superelastic alloy, and has an opening within it slightly smaller than the fastenable portion. The clamp body includes attachment member, which may be in the form of small holes, to which may be applied an external stretching force in a direction and magnitude sufficient to cause the opening to expand elastically to receive the fastenable portion of the article. As the stretching force is released, the opening elastically contracts toward its initial size to clamp upon the fastenable portion. Disclosed also is an instrument attachable to the clamp body for imparting the stretching force to the body.

12 Claims, 4 Drawing Sheets

CLAMP AND METHOD FOR ITS USE

FIELD OF THE INVENTION

The invention relates to the field of clamping and fastening devices, and particularly to such devices as are useful in the field of medicine for the securement of bones and prostheses.

BACKGROUND OF THE INVENTION

In modern surgical techniques involving the placement of prostheses or the holding together of bones and bone fragments, a variety of fasteners are available to the surgeon. Perhaps the most widely used fastener is a bone screw which is threaded into pre-drilled guide holes in various bones and prostheses. See, for example, U.S. Pat. Nos. 5,466,238 and 5,474,553.

Bone screws are the primary mechanical fasteners. They commonly are expensive and must be stocked in a variety of sizes so as to be ready for use when a patient is in the operating theater. Bone screws are invasive, and although they may serve to strengthen a bone by securing a strengthening sheath or rod to the bone, the bone itself becomes weaker as a result of stress shielding. Substantial effort must be taken by a surgeon to properly locate where a bone screw is to be placed, and once a bone screw has been screwed into a bone, the position of the screw cannot be changed. Rather, if a different location is required, a separate hole in the bone must be drilled.

More particularly, in the procedure for stabilizing a fractured bone or fusion site, it is common to use bone screws to secure a plate or rod to the bony structure and to provide interlock between the bone screw and plate or rod. The interlock between the screws and the plate or rod is typically mechanical and involves threaded fasteners, washers, and/or crimped junctions. Sufficient torque or other force must be applied to ensure proper locking and longevity of the interlock. Poor interlock systems may cause the juncture to loosen and fail, resulting in failure of the fracture, fixation or fusion. Hence, the success of interlock devices of this nature are highly dependent on the knowledge and skill of the surgeon.

Other fasteners have involved the use of cements such as the type employed for anchoring implanted hip stems in the proximal femoral intramedullary canal of a patient in the implantation of an artificial hip. Yet other fasteners involve metal cables that are, for example, passed around a splintered or fractured bone to hold the bone pieces in place, the ends of the band being held together by crimping or through use of threaded fasteners.

What is clearly needed is an interlock system that provides a predictable, reliable and consistent interlock for securing structures of metal, plastic, composite and/or ceramic to bone or to themselves. An interlock system is also needed to stabilize a total joint replacement to bone and to secure augments to the implant to accommodate bone loss or bony defects encountered in surgery.

SUMMARY OF THE INVENTION

The present invention provides a clamp which, broadly speaking, is capable of rigidly but releasably fastening to an article that has a fastenable portion of a predetermined shape and size. In the field of medicine, the clamp can be used in connection with a band which encircles a bone to hold bone fragments together, or can be used to clamp together parts of a prosthesis, etc. The clamp comprises an elastic body that preferably is formed at least in part of superelastic alloy. The body has an opening extending within and preferably through it, the opening being sized slightly smaller than the fastenable portion. The clamp includes attachment means to which may be applied an external stretching force in a direction and magnitude to cause the opening to expand elastically sufficiently to receive the fastenable portion. As the stretching force is released, the opening elastically contracts toward its initial size to clamp upon the fastenable portion.

Preferably, the body has a dimension in a first orthogonal direction that is substantially smaller than the dimensions in either of the two other orthogonal directions, the attachment means being positioned to enable the opening to expand in a direction perpendicular to the first orthogonal direction. In one embodiment, the opening extends within the body in a direction perpendicular to the first orthogonal direction, and in another embodiment, the opening extends within the body in a direction parallel to the first orthogonal direction.

The invention has particular utility in the medical field in which it can be employed to hold the ends of an encircling band together to stabilize bone fragments, and to aid in the assembly of various bone prostheses such as pedicle screw devices, trauma fixation devices, external fixation devices, and for securing augments to implants to replace missing bone.

DETAILED DESCRIPTION

Figure 1:
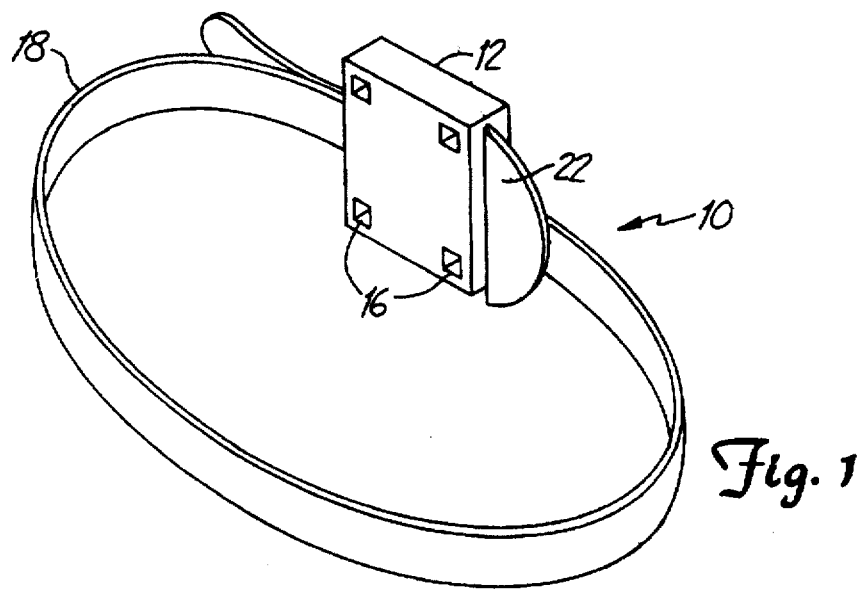
FIG. 1 is a perspective view of a locking device of the invention shown locking together the ends of a band.
Figure 2:
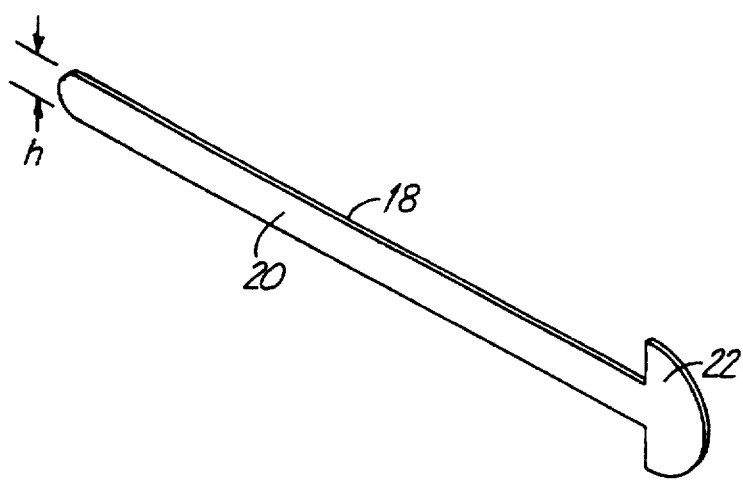
FIG. 2 is a perspective view of a band shown also in FIG. 1.

As will be evident from the description that follows, the clamp of the invention makes use of an elastic clamp body that preferably is formed at least in part, preferably entirely, of superelastic alloy such as nitinol, the body having an opening in it. The elastic characteristic of the body material enables it to be stretched so as to enlarge one or more dimensions of the opening in the plane normal to the axis of the opening to enable the opening to receive a band or other fastenable portion of an article (including several articles that are to be clamped together) that otherwise would not fit through the opening. Upon release of the force tending to enlarge the opening, walls of the opening clamp down upon the fastenable portion to clamp it in place. As used herein, "elastic" as used to refer to the clamp body refers to the capacity of the body to be deformed from an original configuration upon application of an external force and to return toward its original configuration when the force is released.

FIGS. 1–5 describe a clamp of the invention which is employed in holding the ends of a band together. The clamp and band combination is shown as 10 in FIG. 1 as including a clamp body 12 of a generally parallelepiped shape, the body having a thickness dimension "t" in FIG. 3) which is the smallest of the three orthogonal dimensions, the other two dimensions—the height and width—being approximately the same. Extending through the width of the clamp body 12 is a generally rectangular opening 14. Attachment means in the form of holes 16 are formed adjacent the four corners of the clamp body, the holes extending at least partially through the thickness of the clamp body. Into these holes 16 will be inserted the pins of a force-applying device such as that shown in FIG. 6, as will be described below.

A metal band is shown at 18, the band having an elongated body 20 (FIG. 2) of generally rectangular cross section. The band 18 is preferably of uniform dimensions substantially throughout its length, but may have an enlarged section 22 at one end. The dimensions of the band are such that it cannot freely pass through the opening 14 because the height ("h" in FIG. 2) is slightly less than the corresponding height of the opening 14 in the clamp body. The band may be of any appropriate metal such as titanium. Nitinol or other superelastic alloy may be employed as the band material.

Figure 6:
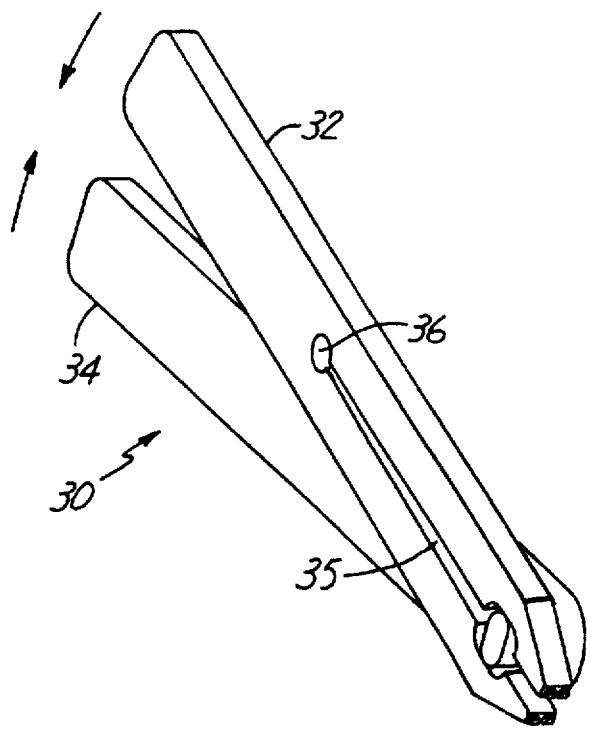
FIG. 6 is a perspective view of a manual, force-generating device for use with clamps of the invention.
Figure 6A:
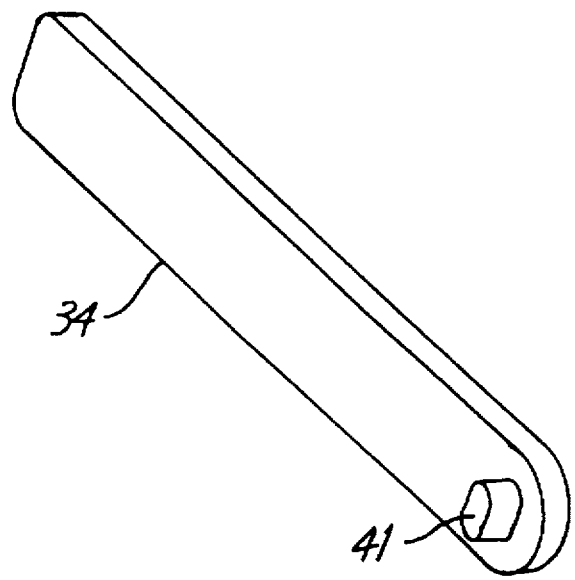
FIGS. 6A and 6B are perspective views of elements of the device shown in FIG. 6.
Figure 6B:
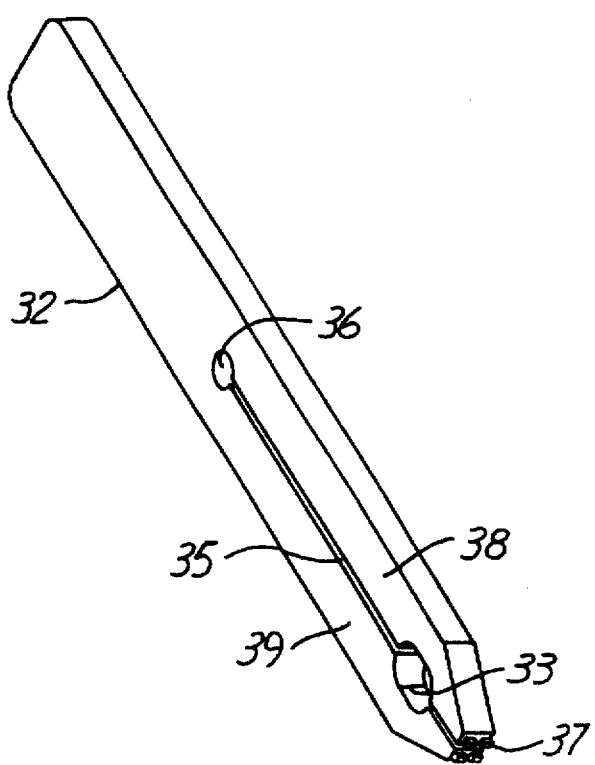

With reference to FIG. 6, a force-generating device 30 can be employed to exert a strong stretching force on the body of the clamp to expand the opening in the clamp body. The device 30 comprises two elongated sections 32, 34. Section 32 has an elongated, forwardly open slot 35 along a portion of its length, the slot terminating rearwardly in a stress-relieving bore 36. Near its forward end, the slot 35 is widened into an elongated opening 33 having a generally oval or racetrack configuration. Section 32 terminates forwardly in a nose portion having forwardly projecting pins 37, 40 oriented and spaced to be received within the attachment holes of the clamp body shown in FIGS. 2 and 3. The pins 37 that project from arm 38 are to be received in the upper two holes of the clamp body, and the pins 40 that project from are 39 are to be received in the lower holes of the clamp body. The holes 16 preferably are rectangular in shape, as are the pins 37, 40, for the purpose of maximizing surface contact between the pins and holes and also for maximizing the shear plane area of the body between the holes and the neighboring edges of the body.

Section 34 has a camming projection 41 extending laterally near its forward end and sized for reception in the oval opening 33 of section 32. Projection 41 also is oval in shape and is sized so that its outer surfaces engage and cam apart the confronting walls of the opening 33 when the rearward portions of sections 32 and 34, which serve as handles, are squeezed together as shown by the arrows in FIG. 6. By squeezing the handles together, the pins 37, 40 are caused to separate, stretching the clamp body of FIG. 3 vertically, as shown in that figure, and thereby slightly expanding the height of the opening 14 sufficiently to receive the band 18. While the opening 14 is thus held in its expanded position, the band may be inserted through the opening until the enlarged potion 22 comes into abutment with the surface of the clamp body adjacent the opening entrance, and the band may thence be passed around a bone, a prosthesis or other articles to be held together or supported, and then may be reinserted through the opening 14, as shown in FIGS. 1 and 4. By releasing the stretching force, the height of the opening 14 elastically contracts in height toward its initial size to clamp strongly and securely against the band portions received in the opening.

It will be understood that the device of FIG. 1, once in place, can be easily adjusted by reinserting the pins 42 of the stretching device, stretching open the opening 14 slightly to enable the band to be loosened, and once the clamping device has been repositioned correctly, the force is removed to again clamp the band securely in the clamp body 12. Also, if the band is made of a superelastic alloy such as nitinol, the band itself can be elastically stretched about a bone or other object to be clamped, with the ends of the band being securely clamped in the clamp body, the band thus exerting continuous clamping pressure on the object.

As explained at greater length below, superelastic alloys may be elastically deformed beyond their so-called Hooke's law region. By forming the clamp body of a superelastic alloy such as nitinol, one may elastically deform the body to a substantial extent, permitting greater dimensional tolerances of the body opening and the article to be clamped in the opening.

Figure 7:
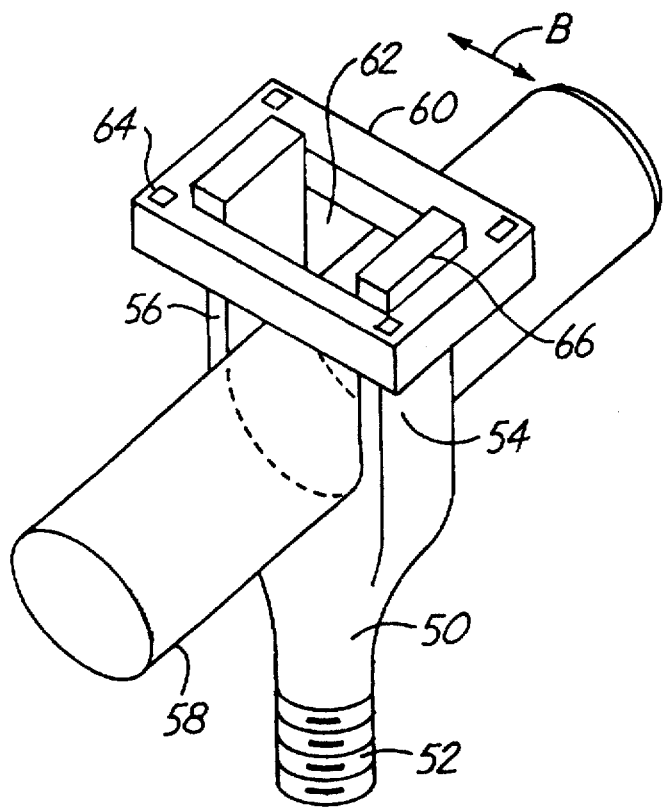
FIG. 7 is a perspective view of a clamp of the invention shown in association with arms of a pedicle screw clamped to a supporting rod.
Figure 8:
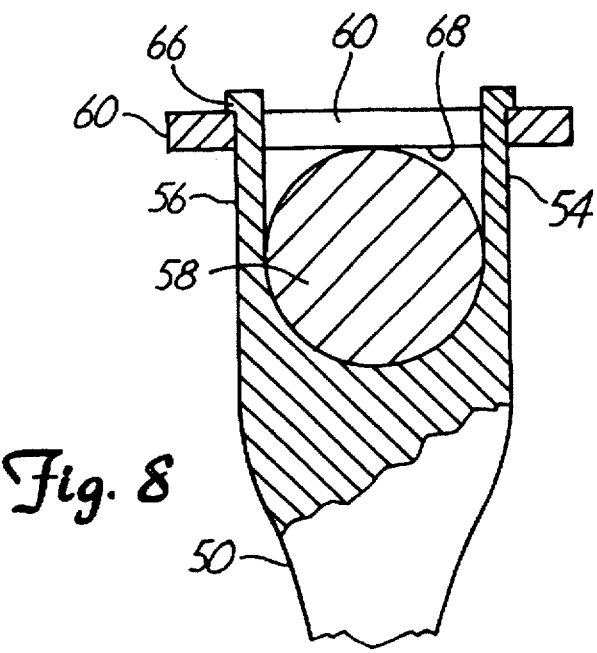
FIG. 8 is a broken-away, elevational view of the device of FIG. 7, shown in partial cross section.

FIG. 7 discloses a pedicle screw at 50. Pedicle bone screws may be placed in multiple vertebral bodies and interconnected with rods to stabilize the spine and promote bony fusion. The interconnecting rods (illustrated at 58) are placed in a suitably designed yoke structure on the head of each pedicle screw. In FIG. 7, the screw 50 has a threaded length 52 and a yoke formed of a pair of spaced arms 54, 56 between which is received the rod 58. As it will be understood from FIGS. 7 and 8, the rod 58 is clamped between the arms 54, 56 when the arms themselves are forced toward one another, and this is the function of the clamp 60, which will now be described.

Figure 3:
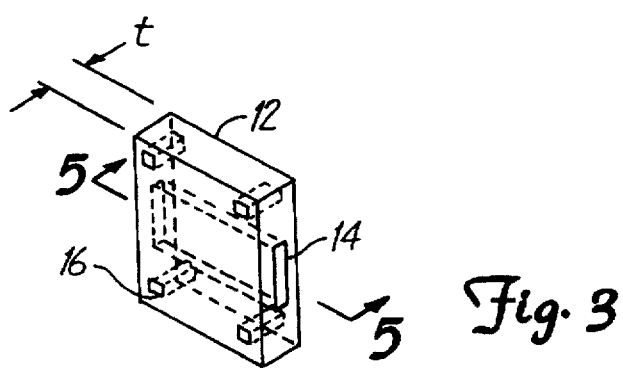
FIG. 3 is a clamp body of the type used in the clamp of FIG. 1.
Figure 4:
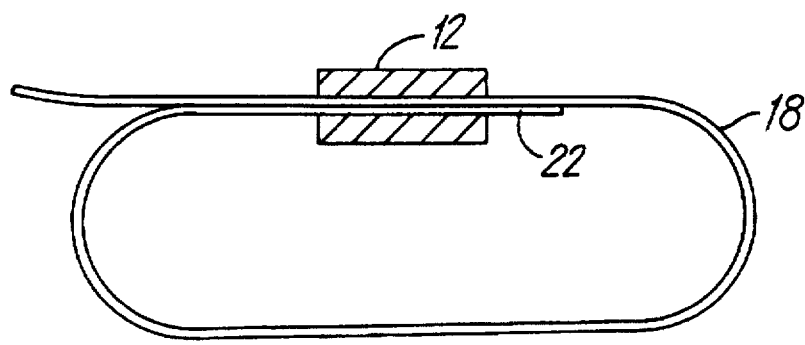
FIG. 4 is a top view of the clamp of FIG. 3, with the clamp body being shown in cross section.
Figure 5:
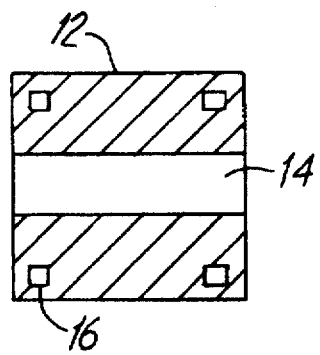
FIG. 5 is a cross-sectional view taken along line 5—5 of FIG. 3.

The clamp 60 is similar to the clamp of FIG. 3 except that the opening 62 for receiving a fastenable portion of an article is formed through the smaller thickness dimension of the clamp body rather than through its somewhat wider width as is the case with the opening 14 in FIG. 3. Fastener holes 64 are formed near the corners of the clamp body 60, and a force generating device such as that shown in FIG. 6 may be employed to stretch the clamp body 60 so as to expand the opening in the direction of the arrow B in FIG. 7. The opening 62 is sized so that it must be expanded in the direction of the arrow B in order to receive the upper ends of both the arms 54, 56. The upper ends of these arms may have slight outwardly offset shoulders 66 as shown best in FIG. 8 to aid the clamp body 60 in locking the arms 54, 56 and the rod 58 together. In any event, once the stretching force is released, the opening 60 elastically contracts toward its initial position and strongly clamps to the ends of the arms 54, 56 causing these arms to also clamp between them the rod 58. Note may also be made in FIG. 8 that the clamp body 60, once in place, has a lower surface 68, which may be positioned to come into downward contact with the rod 58, thus further securing the rod in place.

The invention has particular application for attaching augments to the body of a bone prosthesis implant. For example, in the case of a total knee replacement, augments under the tibial plateau or inside the femoral box are sometimes required to fill in and account for bony defects or missing bone in the supporting bony structure. In one embodiment, an augment is designed with a slot in its implant-facing surface to slide over a cylindrical peg extending from the implant surface where augmentation is needed. A locking band, preferably made of nitinol or other superelastic alloy, is stretched and secured around the augment and prosthesis and is held in place by a clamp body such as that shown in FIG. 3. When released from the stretching force used to stretch the band, the band tends to shorten and to exert a clamping force on the augment, securing it to the implant. Similarly, augments may be readily attached by means of the invention to hip stems or acetabular cups in total hip replacement procedures.

As a further example of utility, trauma fixation devices may be assembled through use of the invention. In an exemplary embodiment, a bone plate of known construction is formed of two or more sections that are linked together by a sliding mechanism. The parts of the sliding mechanism can be secured together against sliding movement by stretching a clamp of the invention so that the sliding mechanism parts are received in the opening in the clamp body. Upon release of the stretching force, the clamp securely locks the sliding mechanism parts together.

As yet another example of use, the invention may be used in connection with external fixation devices often used with fractured bones. External fixation involves placement of percutaneous pins into segments of a fractured bone and connecting the pins to an external structure to stabilize the fractured bone. The external structure employs a clamping mechanism locking the percutaneous pins to connecting rods. The connecting rods are typically telescoping and use clamps to lock the telescoping sections together. A clamp of the invention may be configured to securely clamp together the pins and rods and to clamp together against relative movement the telescoping rod sections.

It will be understood that the stretching force that is applied to the clamp bodies of the invention may be so directed as to enlarge the opening in more than one direction to accommodate various structures to be clamped. For example, stretching forces may be applied to the clamp body in two directions at right angles to each other and perpendicular to the axis of the opening to more or less uniformly enlarge the opening so that a cylindrical rod or tube may be received in the opening. Once the stretching forces are removed, the walls defining the opening squeeze down on the rod or tube with some circumferential uniformity to provide a secure grip.

Although the clamp body may be made of any appropriate elastic material such as polymers, composites, stainless steel and other metals or metal alloys, superelastic alloys are greatly preferred. Superelastic alloys are those alloys that can be deformed to a far greater degree than can other metals and metal alloys without taking a permanent set. Various alloys possess superelastic characteristics. Of these, a near stoichiometric mixture of nickel and titanium, commonly known as "nitinol", is the most widely used and successful. In addition to possessing desirable mechanical characteristics, nitinol also possesses excellent biocompatability.

Superelasticity refers to a phase transition that occurs in a superelastic alloy when a deforming stress is externally applied. Nitinol, as well as other superelastic alloys, (sometimes called shape memory alloys), basically exists in either of two crystallographic forms. Which form the alloy will be in depends upon several variables including ambient temperature, chemical composition and thermomechanical history. Austenite is the parent phase, characterized by a body centered cubic structure. Martensite is a transition phase and is characterized by a monoclinic crystalline structure. Generally, austenite will be present at higher temperatures than will martensite.

Of importance to the present invention, austenite will be transformed into martensite when the alloy is deformed by an external force. The area of the alloy that is thus deformed will remain in the martensite phase as long as the deforming force is maintained. When the stress is relieved, the deformed portion will tend to resume its original shape and in so doing will revert back to the austenite phase. This phenomenon is the basis of superelasticity. The present invention makes use of superelastic alloys that, at the temperature of use (commonly body temperature or ambient temperature), are in the austenite phase and form stress-induced martensite when deformed by an external force. An additional benefit of superelasticity involves the ability of superelastic alloys to undergo great elastic deformation at substantially constant stress. Alloys that are not superelastic commonly exhibit approximate proportionality between increasing stress and resultant strain (Hooke's law) only until plastic deformation begins. If the stress is released after considerable plastic deformation, little shape recovery occurs. Superelastic alloys demonstrate proportionality between stress and strain within the Hooke's law region until a yield stress is reached, but thereafter elastically recoverable further strain occurs at substantially constant stress (as stress-induced martensite is formed). Upon release of the stress, the alloy returns elastically to essentially its original shape.

While a preferred embodiment of the present invention has been described, it should be understood that various changes, adaptations and modifications may be made therein without departing from the spirit of the invention and the scope of the appended claims.

What is claimed is:

1. A clamp for rigidly but releasably fastening to an article having a fastenable portion of a predetermined shape and size, the clamp comprising an elastic body having an opening extending within the body, the opening being sized slightly smaller than the fastenable portion, the clamp including attachment means to which may be applied an external stretching force in a direction and magnitude to cause said opening to expand elastically sufficiently to receive said fastenable portion, whereupon, as said stretching force is released, said opening elastically contracts toward its initial size to clamp upon said fastenable portion.

2. The clamp of claim 1 wherein said body has a dimension in a first orthogonal direction that is substantially smaller than the dimensions in either of the other two orthogonal directions, and wherein said attachment means is positioned to enable said opening to expand in a direction perpendicular to said first orthogonal direction.

3. The clamp of claim 2 wherein said opening extends through said body in a direction perpendicular to said first orthogonal direction.

4. The clamp of claim 3 wherein said article comprises an elongated flat band having a portion along its length defining said fastenable portion, and wherein said opening is sized to permit passage of said fastenable portion through said opening only upon elastically expanding said opening in a direction perpendicular to both the thickness and the length direction of the band.

5. The clamp of claim 4 wherein said opening is of a width, measured parallel to said first orthogonal direction, sufficient to receive at least two thicknesses of said band, whereupon said band may be passed through said opening, about a second article, and back through said opening to clamp onto said second article.

6. The clamp of claim 5 wherein said band is of uniform width and thickness along substantially its entire length.

7. The clamp of claim 6 wherein said band has an enlarged portion at one end restraining said end from passing through said opening when said opening is enlarged.

8. A clamp for rigidly but releasably fastening to an elongated band, a length of the band having a predetermined cross-sectional size and configuration, the clamp comprising a body formed at least in part of superelastic alloy and having an opening extending through the body, the opening being sized slightly smaller than said cross-sectional size of the band, the clamp including attachment means to which may be applied an external stretching force in a direction and magnitude to cause said opening to expand elastically sufficiently to receive said band length, whereupon, as said stretching force is released, said opening elastically contracts toward its initial size to clamp upon said band.

9. The clamp of claim 8 wherein said opening is of a width, measured parallel to said first orthogonal direction, sufficient to receive two thicknesses of said band, whereupon said band may be passed through said opening, about an object to be grasped, and back through said opening to clamp onto said object.

10. The clamp of claim 2 wherein said opening extends through said body in a direction parallel to said first orthogonal direction.

11. The clamp of claim 10 wherein said article has a pair of arms having end portions defining fastenable portions, the end portions being spaced apart by a distance enabling them both to be received within said opening only upon elastically expanding said opening in a direction perpendicular to said first orthogonal direction, whereby, upon release of said stretching force, said arm end portions are locked in said opening.

12. The clamp of any one of claims 1 through 11 wherein said clamp body is formed at least in part of superelastic alloy.

* * * * *